United States Patent [19]

Holtkamp

[11] Plant 4,774

[45] Oct. 6, 1981

[54] AFRICAN VIOLET PLANT

[76] Inventor: Reinhold Holtkamp, Werther Strasse 112, D-4294 Isselburg, Fed. Rep. of Germany

[21] Appl. No.: 172,397

[22] Filed: Jul. 25, 1980

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet known by the cultivar name Utah, characterized by its deep blue flower color, vigorous, compact and uniform growth habit, strong upright stems each carrying up to 15 non-dropping flowers, and by its heavy golden yellow pollen sacs which provide a pleasant contrast with the deep blue flowers.

1 Drawing Figure

The present invention comprises a new and distinct cultivar of African violet plant, botanically known as *Saintpaulia ionantha,* and hereinafter referred to by the cultivar name Utah.

The new cultivar was referred to during the breeding and selection process by the designation D 154/5, and is a product of a planned breeding program. The basic objective of the breeding program was to create a new African violet cultivar having a compact habit, and a deep blue corolla.

The new cultivar was originated from a cross made in a controlled breeding program in Isselburg, West Germany. The female, or seed parent was a cultivar designated XVIII 1233, a deep blue single. The male, or pollen parent was Evelyn, disclosed in U.S. Plant Pat. No. 4,154.

The new cultivar Utah was discovered and selected by me as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and are retained through successive generations of asexual reproduction.

Utah has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of Utah, which in combination distinguish the African violet as a new and distinct cultivar:

1. Vigorous and uniform growth habit.
2. Compact habit.
3. Strong upright flower stems carrying deep blue non-dropping flowers.
4. Very floriferous, carrying up to 15 flowers per stem.
5. Heavy golden yellow pollen sacs, providing a pleasant contrast with the deep blue blossoms.

The new cultivar is most similar to the cultivar Wisconsin, disclosed in my U.S. Plant Pat. No. 4,353. Utah is principally distinguished from Wisconsin by its deep blue blossom color and floriferous habit, its more prominent pollen sacs, more compact growth habit, and by its deeper green leaves. When compared with the paternal parent Evelyn, Utah has a much deeper blue flower color, and deeper green leaves.

The accompanying photographic drawings shows a typical specimen plant of the new cultivar. The colors appearing in the photograph are as true as possible with color illustrations of this type.

In the following description, color references are made to the Horticultural Colour Chart (HCC) issued by Wilson Colour Ltd., except where general colors of ordinary significance are referred to. Color values were taken under natural light conditions approximately midday in Isselburg, West Germany.

Botanical classification: *Saintpaulia ionantha,* Ramat. cv. Utah.

Parentage:

*Male parent.*—Evelyn (U.S. Plant Pat. No. 4,154).

*Female parent.*—XVIII 1233, a deep blue single.

Propagation: The new cultivar holds its distinguishing characteristics through successive propagations by leaf cuttings.

Plant: From 8 cm. to 10 cm. tall when grown in pots, and approximately 25–30 cm. in diameter when fully grown.

Leaves:

*General form.*—Heart-shaped.

*Diameter.*—Up to 65–75 mm.

*Texture.*—Soft, hairy, slightly serrated.

*Aspect.*—Velvety, slightly shiny.

*Veins.*—Upperside, well visible; underside well-pronounced and glassy; underside of younger leaves brownish-purple and sightly hairy, mature leaves brownish-green.

*Color (upperside).*—HCC Parsley green 00962.

*Color (underside).*—HCC Willow green 000862/2.

*Petiole.*—Young leaf light brown, hairy.

Flowers:

*Buds.*—Ball-shaped, 5–7 mm. just before opening; 7–12 buds per stem.

*Sepals.*—Color: Brownish-green. Calyx: Flat, funnel-shaped. Aspect: Spear-shaped, hairy. Peduncle: Brown, hairy, short, wire-like.

Individual flowers:

*Size.*—Between 35–45 mm.

*Color.*—Upperside: Victoria violet 738 and darker; Underside: Victoria violet 738/2. Upperside of older flowers methyl violet 39, underside 39/1.

*Borne.*—Flower stem carries 7–12 flowers on short strong peduncles; flowers occasionally display an additional small petal in the center of the flower.

*Shape.*—Conventional violet-shaped blossom; 2 small and 3 large petals.

*Corolla.*—Profuse and compact, setting centrally above leaves.

*Flowering time.*—6–7 weeks after parting first flowers appear; 8–10 weeks to full-flowering, saleable plant.

Reproductive organs:

*Anthers.*—2, composed of 4 cells, with seed capsule pushed slighty through; color sulphur yellow/1.

*Filaments.*—4–5 mm., base about 3 mm., purple, changing into 2 mm. light green.

*Styles.*—7 mm., purple; base of ovary light green, hairy.

*Pollen color.*—HCC Dresden yellow 64/2.

Roots: White when young and active; normally developed.

Disease resistance: Good as experienced to date.

General observations: Utah is a very uniform growing and floriferous variety with upright flower stems carrying up to 15 deep blue blossoms which do not fade when mature. Flowers do not drop but dry off on the stem, thus, avoiding butritis in the full flower head. Corolla is full and compact, situated centrally and tightly above the leaves.

I claim:

1. A new and distinct cultivar of African violet known by the cultivar name Utah, as described and illustrated, and particularly characterized by its deep blue flower color, vigorous, compact and uniform growth habit, strong upright stems and carrying up to 15 non-dropping flowers, and by its heavy golden yellow pollen sacs which provide a pleasant contrast with the deep blue flowers.

* * * * *

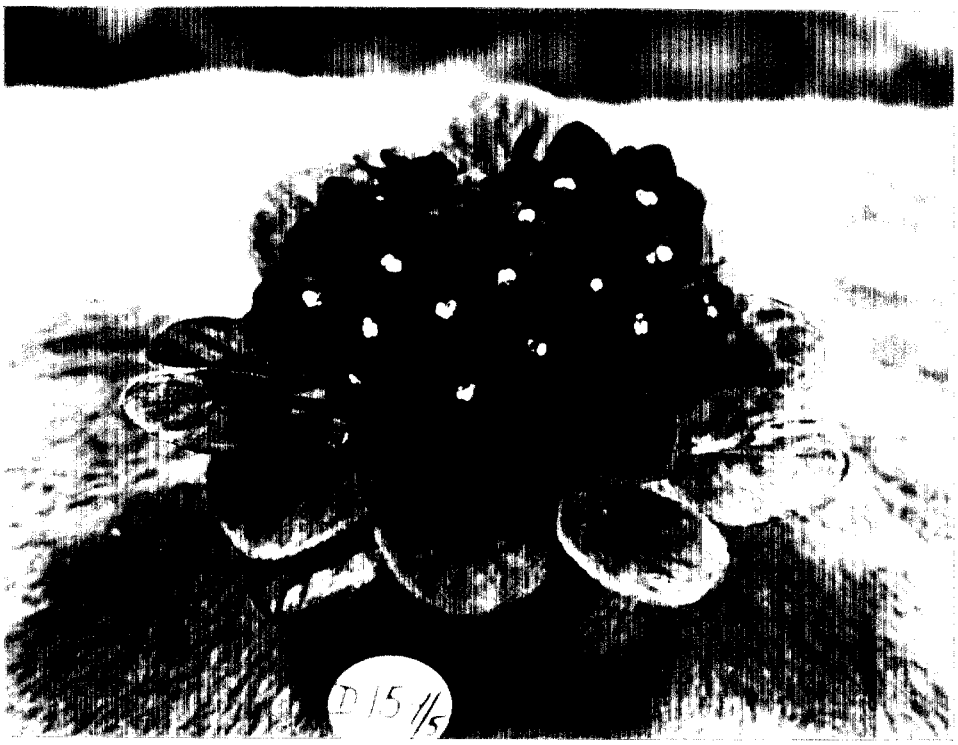
D 15 1/5